United States Patent [19]
Novak

[11] Patent Number: 5,935,862
[45] Date of Patent: Aug. 10, 1999

[54] MICROSPOT TEST METHODS AND FIELD TEST KIT FOR ON-SITE INSPECTIONS OF CHEMICAL AGENTS

[75] Inventor: Thaddeus J. Novak, Bel Air, Md.

[73] Assignee: The United States of America as represented by the Secretary of the Army, Washington, D.C.

[21] Appl. No.: 08/763,181

[22] Filed: Dec. 11, 1996

Related U.S. Application Data

[60] Provisional application No. 60/010,271, Jan. 19, 1996.

[51] Int. Cl.$^6$ .......................... G01N 33/20; G01N 30/90
[52] U.S. Cl. .......................... 436/104; 436/162; 436/808; 422/61; 422/100; 422/101; 422/68.1
[58] Field of Search ..................... 436/103–105, 436/161–162, 808; 422/99–104, 68.1, 69, 61

[56] References Cited

U.S. PATENT DOCUMENTS

| | | | |
|---|---|---|---|
| 4,120,754 | 10/1978 | Barendsz et al. | 435/20 |
| 4,740,468 | 4/1988 | Weng et al. | 435/805 |
| 4,772,551 | 9/1988 | Hart et al. | 436/518 |
| 4,971,803 | 11/1990 | Li et al. | 424/450 |

*Primary Examiner*—Lyle A. Alexander
*Attorney, Agent, or Firm*—Ulysses John Biffoni; Edward L. Stolarun

[57] ABSTRACT

Methods of rapidly detecting the presence of chemical warfare agents, chemical warfare agent precursors and degradation products thereof are disclosed. The methods are useful, for example, in screening chemical sample unknowns in Chemical Warfare Convention (CWC) inspections. The methods include contacting a sample suspected of containing chemical warfare agents, precursors, chemical warfare agent degradation products and mixtures thereof with a sufficient amount of a chromatographic adsorbent material and a sufficient amount of a chromogenic detector reagent whereby a chromogenic indicator is formed when the sample contains chemical warfare agent, precursors or degradation product thereof. A kit useful for carrying out the method is also disclosed. The test methods can be used, either alone or in combination with thin-layer chromatography, to provide presumptive evidence for CWC analytes without actually identifying any of the components of the samples.

26 Claims, No Drawings

MICROSPOT TEST METHODS AND FIELD TEST KIT FOR ON-SITE INSPECTIONS OF CHEMICAL AGENTS

This application is a nonprovisional continuation of provisional application Ser. No. 60/010,271, filed Jan. 19, 1996.

GOVERNMENT INTEREST

The invention described herein may be manufactured, licensed, and used by or for the U.S. Government.

BACKGROUND OF THE INVENTION

1. Field of the Invention

This invention relates to methods and kits for detecting the presence of chemical warfare agents and degradation products thereof More particularly, the invention relates to an accurate and rapid method of detecting the presence of chemical warfare agents, precursors of chemical warfare agents, and degradation products of chemical warfare agents in a sample.

2. Description of the Prior Art

Over the years, various highly toxic chemical warfare agents (CWA's) have been developed and stockpiled by several nations. In view of the biological hazards associated with CWA's and degradation products thereof, chemical warfare conventions (CWC's) have been developed by certain countries. These CWC's monitor, identify and, if necessary, dispose of CWA's which are not in compliance with the convention. As a result of the convention, it is often necessary to conduct inspections of various sites in order to assure compliance.

On-site analysis of sample unknowns in CWC verification inspections is preferred to off-site analysis. Some reasons for this preference include:

a) existing agreements call for on-site analysis;

b) when samples are analyzed on-site, ambiguities can be resolved during the inspection;

c) since unknown samples are not removed from the inspection site, contamination and cross-contamination of samples during travel to off-site laboratories cannot occur; and d) since ambiguities will be resolved on-site during the inspection, the inspection report that is completed at the end of the inspection would not be subject to challenge.

One of the requirements for the screening methods employed in on-site inspections is that they be essentially non-intrusive. Every possible effort must be made to utilize analytical methods that do not allow the loss of sensitive corporate or governmental information during on-site inspections. Reagent-based screening methods are attractive because many tests can be run in a short period of time and, since they give only a positive or negative response, they are capable of providing presumptive evidence for a prohibited substance in a sample without revealing the identity of any of the components in the sample.

Consequently, a number of reagent based screening tests have been included in the initial operating capability (IOC) for the on-site CWC verification inspections. Unfortunately, these tests do not have a high degree of detection specificity.

Classical spot tests are usually carried out in a porcelain spot plate containing depressions to which detector reagents are added. In practice, a small amount of a test sample, hereinafter, "a sample unknown" is placed in one or more of the depressions of the spot plate. Small quantities of one or more reagents are then added to it. A positive test is usually signified by a color change. As many as 12 different spot tests can be carried out in a small (3.5×4.5 inch) spot plate. In most cases, the lower limit of detection is in the 1–100 microgram range. More sensitive testing methods for on-site inspections would be welcomed.

In view of the advantages of rapidly and accurately identifying the presence of CWA's and associated by-products, and further in view of the need to address the shortcomings associated with currently available detection methods, there is still a need for new and improved detection methods and kits. In particular, there remains a need for rapidly and accurately detecting submicrogram quantities of CWA, CWA precursors and related degradation byproducts. The present invention addresses these needs.

SUMMARY OF THE INVENTION

In one embodiment, the invention provides a method of detecting the presence of chemical warfare agents, chemical warfare agent precursors and degradation products thereof, (hereinafter "analytes"). This method includes the steps of:

contacting a sample suspected of containing a member of the group consisting of chemical warfare agents, chemical warfare agent precursors, chemical warfare agent degradation products and mixtures thereof with a sufficient amount of a chromatographic adsorbent material and a sufficient amount of a chromogenic detector reagent, so that a chromogenic indicator is formed when the sample contains a member of the aforementioned group of chemical warfare agents.

In another embodiment of the invention there is provided a kit for chromogenically detecting the presence of chemical warfare agents, chemical warfare agent precursors and degradation products thereof. The kit includes:

a) means for obtaining a sample suspected of containing a member of the group consisting of chemical warfare agents, chemical warfare agent degradation products and mixtures thereof, b) a sufficient amount of a chromatographic adsorbent material c) a sufficient amount of a chromogenic detector reagent, d) means for reacting the sample, chromatographic adsorbent material and chromogenic detector reagent so that a chromogenic indicator can be formed when the sample contains of the aforementioned member of the group.

As a result of the invention, it is possible to accurately screen a large number of samples during a limited time inspection period. For example, as many as 30–40 samples can be screened in a short (4–5 hour) period. The present invention also provides increased detection sensitivity and accuracy over the tests of the prior art. The detection sensitivity is improved by an order of magnitude or more over existing methods by applying the sample unknown dissolved in an appropriate solvent to a small piece of thin-layer chromatography media using a microcapillary tube. The improved accuracy is achieved by improved detection specificity which in turn reduces the likelihood of false positive tests and the susceptibility of the tests to interferences. After a series of on-site spot tests are completed, only samples found to be suspect will need to be subjected to analysis by GC-mass spectrometry.

DETAILED DESCRIPTION OF THE PREFERRED EMBODIMENT

The invention provides methods of detecting the presence of chemical warfare agents, chemical warfare agent precursors and degradation products thereof which comprises contacting a sample suspected of containing a member of the group consisting of chemical warfare agents, chemical warfare agent precursors, chemical warfare agent degradation products and mixtures thereof with a sufficient amount of a chromatographic adsorbent material and a sufficient amount of a chromogenic detector reagent whereby a chromogenic indicator is formed when a sample contains a member or analyte of the group.

The sample is preferably in the form of a solution. In one aspect of the invention, the solution is obtained by wiping a suspected surface with a polyester or similar type wipe or cloth and thereafter extracting the materials present on the wipe with a suitable organic solvent such as acetone, dichloromethane, hexane, etc. Alternatively, a soil sample can be eluted to obtain the liquid sample for analysis. A still further aspect includes combining an aqueous sample suspected of containing the CWA analyte with an immiscible solvent which is capable of extracting the CWA analyte believed to be therein.

Once the liquid extract has been formed, and the extract has been concentrated by evaporation, the method is preferably carried out using a capillary or microcapillary tube to draw up and deliver the sample to the chromatographic adsorbent. In this regard, the contacting step includes delivering or reacting from about 0.1 microliters (est. 0.05 mm diameter microcap opening) to about 10 microliters (est. 0.7 mm diameter microcap opening) of the sample with the chromatographic adsorbent material. Preferably, the sample size is from about 0.5 microliters (est. 0.1 mm diameter microcap opening) to about 5 microliters (est. 0.4 mm diameter microcap opening) and most preferably, the sample is from about 1 microliter (est. 0.2 mm diameter microcap opening) to about 3 microliters (est. 0.25 mm diameter microcap opening). If desired, the microcapillary tube can be held with commercially available holders or forceps.

The chromatographic adsorbent material is preferably a thin-layer chromatography plate such as those commonly found in the art containing a silica gel, glass backed thin layer chromatography sheet. A non-limiting list of suitable TLC strips which can be used in carrying out the invention include MK6F Silica Gel 60A TLC plates, glass backed (1"×3"plates), layer thickness 250 microns, Cat. #4861-110 from Whatman, Inc., Clifton, N.J. 07014; Silica Gel F-254TLC media, plastic backed, layer thickness 0.25 mm, Cat #5775 from E. M. Laboratories, Elmsford, N.Y. 10523; Silica Gel F-254 TLC media, aluminum backed, layer thickness 0.2 mm, Cat #5539 from Alltech Associates, Deerfield, Ill. 60115; Silica Gel TLC media, plastic backed, layer thickness 100 microns, Product Number 13179, Cat. #4G 6801, Eastman Kodak Co., Rochester, N.Y. 14650; Instant Thin Layer Chromatography Polysilicic Acid Gel Impregnated Glass Fiber Sheets with Fluorescent Indicator, Product Number 51435, Gelman Instruments, Ann Arbor, Mich. 48106; Instant Thin Layer Chromatography Sheets, Type SG, Product Number, 61886, Gelman Instrument Co., Ann Arbor, Mich. 48106; TLC Plates, Silica Gel 60 F-254, aluminum backed, layer thickness 0.2 mm, Product #37360, Catalog #Z19,329-1, Aldrich Chemical Co., Milwaukee, Wis. 53233; Silica Gel IB Flexible (plastic backed) Sheets for Thin Layer Chromatography, layer thickness 250 microns, Product Number 4462-02, J. T. Baker, Inc., Phillipsburg, N.J. 08865; Aluminum Oxide IB Flexible (plastic backed) Sheets for Thin Layer Chromatography, layer thickness 200 microns, Product Number 4466-00, J. T. Baker, Inc., Phillipsburg, N.J. 08865; MKC18F Reversed Phase TLC plates, glass backed (1"×3"plates), layer thickness 200 microns, Cat. #4803-110 from Whatman, Inc., Clifton, N.J. 07014.

If the TLC sheets used are those which are commercially available, they can be scored into small sample areas within the sheet, i.e. ½ inch ×½ inch or a similar size. The scoring of the plate reduces the likelihood that the liquid detector reagent applied in one spot test will creep into the sections reserved for other spot tests. Alternatively, the method can be carried out using TLC sheets specifically made to carry out the spot tests of the present invention.

After a period of about 1 minute, the combination of sample and chromatographic adsorbent material is treated with a sufficient amount of a chromogenic detector reagent such as bromcresol green, 7,7,8,8-tetracyanoquinodimethane (TCNQ), gold chloride (without NaOH), gold chloride/NaOH solution, 4-(4"-nitrobenzyl) pyridine/NaOH, cholinesterase/indoxyl acetate, sodium pyrophosphate peroxide/aromatic amine, o-dianisidine/sodium perborate, potassium bismuth iodide, 1,3-diisonitrosoacetone guanidinium salt, bis(diethylamino) benzophenone oxime, bis(diethylamino)benzophenone, bis(dimethylamino)thiobenzophenone, phenylazoformic acid 2-diphenylhydrazide, diphenylcarbazone, diphenylthiocarbazone, mercuric salt, diethyldithiocarbamic acid silver salt, 2, 2"-dithiobis(5-nitropyridine), molybdenum oxide in sulfuric acid, ammonium molybdate, iodine/starch, and sulfuric acid (4M). This is only a non-limiting partial list of reagents that can be used in the process described herein.

It is expected that one drop of the detector reagent(s) will be sufficient in order to obtain a result. In tests where two detector reagents are added in sequence, the second detector reagent should be added about two minutes (or more) after the first reagent. In some tests heat is used to accelerate the reaction of a detector reagent with the analyte. If the test is positive, a small spot within the reagent spot on the TLC sheet changes color, often instantaneously, but with low analyte levels may require 15–30 seconds. Furthermore, since the level of analyte appears to be related directly to the size of the color change within the spot, quantification of the analyte levels may be possible. The color changes are visible when most of the analytes are detected at the 10 ng level. One of the analytes can also be detected at the 1 ng level.

It has been surprisingly found that detection sensitivity can be improved by an order of magnitude or even greater if the sample unknown was dissolved in an appropriate solvent and then applied to a small piece of thin-layer chromatography media using a microcapillary tube. Thus, for purposes of the present invention, the methods of the present invention are referred to as "micro spot tests" due to the minute quantities of analyte that are detectable compared with spot tests carried out using the techniques of the prior art. Indeed, the methods of the present invention are capable of detecting the presence of chemical warfare agents or degradation products thereof in the 1–100 nanogram range. While applicants are not bound by theory, it is believed that the increased sensitivity is due at least in part to the fact that the analyte undergoes chromatography when a solution of the analyte is applied with a microcapillary tube to a piece of TLC media, i.e., a solid support coated with a thin layer of chromatographic adsorbent.

An illustrative manner of carrying out the methods of the present invention is provided below:

A sample suspected of containing the analyte methylphosphonic acid is prepared by forming an acetone eluate from a polyester wipe. A microcapillary tube is used to draw up about 1 microliter of the sample and the end of the capillary tube is touched to a piece of TLC medium. The analyte solution wetted the adsorbent layer and migrated by capillary action. Afterward, the TLC medium was allowed to dry and a drop of Bromcresol Green reagent was added. This caused a small yellow spot to be produced in a large dark blue spot (background). This indicated that all of the acid was retained within the inner circle. The acid is retained near the spotting point due to its strong interaction with the chromatographic adsorbent. Since the analyte collects in a small area near the spotting point when the method of the present invention is used, it is possible to detect minute quantities of the analyte. In order to concentrate the analyte in the most compact spot, the solution of the analyte must exit from the microcap, and in doing so, contact only the surface of the thin-layer chromatographic media that comes in contact with the tip of the microcap. When this technique is used, the analyte solution will exit from the microcap by capillary action.

(If the microcap is not kept in contact with the surface of the chromatographic media, a droplet larger than the diameter of the microcap may form. When a droplet larger than the diameter of the microcap forms and and then comes in contact with the thin-layer chromatograpic media, the solution will wet a large area and the analyte will not concentrate in a compact spot. Consequently, the detection sensitivity of the test will be poorer than that obtained using the method described in the previous paragraph).

Table 1 contains a list of compounds that are a representative of the Priority 1 Analytes which can be detected by the processes of the present invention. This list represents a number of analytes which would be expected to be found in an on-site CWC verification inspection. It will be understood by those of ordinary skill in the art that those analytes not specifically mentioned but known are also included herewith and that the new analyses for these analytes would be handled in the same way as analytes that are listed.

TABLE 1

PRIORITY 1 ANALYTES

| COMPOUND | SYNONYM |
| --- | --- |
| ethyl N,N-dimethylphosphoramidocyanate | GA |
| isopropyl methylphosphonofluoridate | GB |
| pinacolyl methylphosphonofluoridate | GD |
| cyclohexyl methylphosphonofluoridate | GF |
| O-ethyl S-(2-diisopropylamino)ethyl methylphosphonothiolate | VX |
| bis(2-chloroethyl)sulfide | HD |
| bis[2-(2-chloroethylthio)ethyl]ether | T |
| 2-chlorovinyldichloroarsine | L |
| methylphosphonic difluoride | DF |
| ethyl 2-(diisopropylamino)ethyl methylphosphonite | QL |
| isopropyl methylphosphonic acid | IMPA |
| pinacolyl methylphosphonic acid | PMPA |
| cyclohexyl methylphosphonic acid | CMPA |
| methylphosphonofluoridic acid | MPFA |
| methylphosphonic dichloride | DC |
| S-(2-diisopropylamino)ethyl methylphosphonothioic acid | EA 2192 |
| ethyl methylphosphonic acid | EMPA |
| O-ethyl methylphosphonothioic acid | EMPTA |
| 1,4-dithiane | DITHIANE |
| 2-chlorovinylarsenious oxide | L-OXIDE |
| methylphosphonic acid | MPA |

In another aspect of the invention, there is provided a method wherein by using two or more micro spot tests in combination, a more specific indication of the analytes found in a sample unknown can be determined. This, in effect, amounts to screening samples with a much finer mesh screen than is now available in the screening kits presently available. In addition, by using a series of spot tests, the artisan is able to accumulate evidence for or against the presence of a Priority 1 Analyte in the sample without actually identifying any of the components of the sample. This is important because the acceptance of the on-site screening procedures by the Chemical Industry will ultimately depend on using methodology that minimizes or eliminates the need for subjecting samples unnecessarily to sophisticated, and potentially more intrusive, analytical methods.

If a sample unknown gives positive tests for one or more Priority 1 Analyte, TLCs could be run to determine if the suspect sample is a mixture, and to obtain Rf value(s) of the suspect analyte(s). For example, the TLC data can show the relative positions (from which Rf values are obtained) for spots resulting from e.g. multiple phosphonic acids and dithiane. The data can be obtained using a procedure similar to that developed by Sass and Ludemann for the separation of phosphonic acids, see *J. of Chromatography*, 187, 447–452 (1980), the contents of which are incorporated herein by reference. It is also noteworthy to mention that the shape of a spot on the TLCs and the rate at which the spot becomes colored when contacted by the visualizing reagent may also help to indicate which analyte is present. For example, a characteristic of the EMPTA spot is that it produces spots that have a long tail. Another characteristic of the EMPTA spot is that it changes color, going rapidly from colorless to brown when the TLC is exposed to iodine vapor. While the spot test data and the TLC data together are not sufficient to identify the components of the unknown sample (which nonetheless is a desirable feature for the screening tests), it is clear that the methods of the present invention can provide a considerable amount of evidence for the presence (or absence) of Priority 1 Analytes in a suspect sample.

Table 2 contains data that show how three of the micro spot tests can be used in combination to accumulate presumptive evidence for the presence of several different Priority 1 Analytes. TLC data can also be used in combination with the micro spot tests to supplement the spot test data and further improve detection specificity. The sample unknown for the micro spot tests is one that would contain one of the following Priority 1 Analytes: MPA, EMPA, IMPA, PMPA, and dithiane.

The data in Table 2 indicate that the response patterns from the three different spot tests can be used to distinguish dithiane and EMPTA from each other, and from MPA and several alkyloxy methylphosphonic acids that are also Priority 1 Analytes. A positive test result in the Bromcresol Green Test indicates that an acidic substance, which could be MPA, or one or more alkyloxy methylphosphonic acid, is in the sample. If the positive test with Bromcresol Green is combined with positive tests with TCNQ (7,7,8,8-tetracyanoquinodimethane) and gold chloride/NaOH, the response pattern indicates that EMPTA may be present, but not dithiane, MPA or the alkyloxy methylphosphonic acids. A positive test with Bromcresol Green in combination with negative tests with TCNQ and gold chloride/NaOH indicates that a sample might contain MPA or one or more alkyloxy methylphosphonic acids, but not EMPTA or dithiane. Negative tests with Bromcresol Green and TCNQ combined with a positive gold chloride/NaOH test indicate that the sample may contain dithiane, but none of the phosphorus acids. Detection specificity is further improved when two or more tests are used in combination because different tests for the same analyte have different interference profiles.

TABLE 2

Results of Micro Spot Tests for Some Priority 1 Analytes
Reagent(s) for Micro Spot Test

| Analyte | Bromcresol Green | TCNO | Gold Chloride/NaOH |
|---------|------------------|------|--------------------|
| MPA     | +                | −    | −                  |
| EMPA    | +                | −    | −                  |
| IMPA    | +                | −    | −                  |
| PMPA    | +                | −    | −                  |
| EMPTA   | +                | +    | +                  |
| DITHIANE| −                | −    | +                  |

Without additional data from other tests, however, the three spot tests used to obtain the data for Table 2, will not indicate if the unknown is a single substance or a mixture, and they will not indicate which phosphorus-containing acids) may be present in the sample. Thus, TLC could be employed to provide more definitive results.

In another aspect of the invention there is provided a micro spot test for determining the presence of alkyloxy methylphosphonic acids. The method depends upon first converting the phosphonic acid into a cholinesterase inhibitor (CI) and thereafter using an existing test to determine if a cholinesterase inhibitor was formed in the conversion reaction. One such existing test for determining the presence of a CI is found in the the U.S. Army M-272 Detector Kit for water borne chemical agents.

The procedure involves a reaction of an alkyloxy methylphosphonic acid (a non-inhibitor) with a dehydrating agent [e.g. 1,3-dicyclohexylcarbodiimide, 1,3-diisopropylcarbodiimide, or an acid chloride and base (e.g., alkyloxy methylphosphonochloridate and triethylamine)] which causes the elimination of a molecule of water from two molecules of the acid, and thereby producing an acid anhydride or "pyro acid" which is a cholinesterase inhibitor and can be detected. For example, the nerve agent detector ticket from the U.S. Army M-272 Detector Kit for Waterborne Chemical Agents is then used to determine if a cholinesterase inhibitor was formed in the reaction. This is done by placing the portion of the detector ticket that contains cholinesterase in contact with the portion of the TLC strip that contains the product of the reaction for a 3-minute period, and then proceeding with the normal procedure for tests with the M-272 detector ticket. The foregoing method is able to provide a detection sensitivity of from about 100 ng to 40 micrograms, depending on which phosphonic acid is present in the sample. The following non-limiting examples serve to illustrate the invention.

EXAMPLE 1

Micro Spot Test for Methylphosphonic Acids Using Bromcresol Green

DETECTION PRINCIPLE

A positive test is the appearance of a yellow spot in a larger blue spot. The control (analyte level =0) and negative tests are indicated by a blue spot that does not contain a yellow center. The color change that is observed in a positive test is due to the difference in the pH of the analyte (pH 3 and above) and the solid support (pH>5). At pH 3.8 and below, bromcresol green is yellow, and at pH 5.4 and above it is blue. The method described herein could be used for detecting other organic acids as well.

DETECTOR REAGENT: Bromcresol Green (0.04% in ethanol).

PROCEDURE FOR PREPARING THE DETECTOR REAGENT

The bromocresol green reagent is available from Aldrich Chemical Company. Transfer 2 ml of the reagent into a 3-ml plastic dropping bottle, replace the tip and screw on the cover.

SOLVENT FOR THE ANALYTE: An organic solvent (e.g. acetone, dichloromethane, hexane)

PREFERRED SOLID SUPPORT: MK6F Silica Gel 60A Glass Backed TLC Sheets, Clifton, N.J.

ANALYTES DETECTED WITH THIS TEST methylphosphonic acid (MPA), methylphosphonofluoridic acid (MPFA), ethyl methylphosphonic acid (EMPA), isopropyl methylphosphonic acid (IMPA), pinacolyl methylphosphonic acid (PMPA), cyclohexyl methylphosphonic acid (CMPA), O-ethyl methylphosphonothioic acid (EMPTA).

DETECTION LIMIT FOR CWC ANALYTES

MPA, EMPA, IMPA, PMPA, CMPA, EMPTA, and MPFA are detectable at the 100 ng level (i.e. when a 1 microliter aliquot of an acetone solution containing 0.01%, or more of analyte is spotted on preferred solid support using a microcapillary tube).

EMPA, IMPA, CMPA, PMPA and EMPTA are also detectable at the 10 ng level (i.e. when a 1 microliter aliquot of a dichloromethane solution containing 0.001% or more of analyte is spotted on the preferred solid support using a microcap).

EQUIPMENT AND MATERIALS a. Locking forceps or spotting bulb assembly for holding microcap (e.g. cat. #20-99, Analtech, Newark, Del.)
b. Microcap, 1-microliter (e.g. cat. #20-01, Analtech)
c. Dropping Bottle, 3-ml capacity, (e.g. cat. #211630, Wheaton, Millville, N.J.)
d. 0.04% Bromcresol Green in Ethanol, cat. #B-7382, Sigma Chemical Co., St. Louis, Mo.)
e. MK6F Silica Gel 60A Glass Backed TLC Sheets or equivalent (e.g. cat. #4861-110, Whatman Inc., Clifton, N.J.)
f. Acetone (e.g. cat. #GC60032-4, Baxter Healthcare Corp., Burdick and Jackson Div., Muskegon, Mich.)
g. Pencil

PROCEDURE

1. Score a 1×3 inch TLC plate into twelve 0.5×0.5 inch sections with a pencil.
2. Lock a 1-microliter microcap in the tip of the locking forceps.
3. Place tip of microcap in a sample of pure acetone (or other solvent for the test) and wait a few seconds for the solvent to be drawn by capillary action to fill the microcap.
4. Place the tip of the microcap in contact with the silica gel surface of the solid support near the center of one of the 0.5×0.5 inch sections. This is the "control" (analyte level =0) spot.
5. Wait a few seconds for the solvent to evaporate.
6. Using a new microcap, for each sample, spot a different sample solution in each of the remaining 0.5×0.5 inch sections of the plate and solvent to evaporate.
7. Using the dropping bottle, add I drop of the bromocresol green to each spot.
8. Observe the plate for the appearance of positive tests. A positive test is indicated by the appearance of a small yellow spot in a large green (wet) or blue (dry) spot. A positive detection signal appears within 1–2 seconds and the colors remain stable for at least several hours.

PURPOSE AND APPLICATIONS

This micro spot test method is suitable as a field test for detecting analytes containing a phosphonic acid group. It provides evidence for or against the presence of CWC analytes in a sample unknown. The test can be used alone or in conjunction with other micro spot tests that detect other functional groups in the sample unknown. When two or more micro spot tests are used in combination, the detection specificity for target CWC analyses is increased compared with the result of a single test.

EXAMPLE 2

Micro Spot Test for O-Ethyl Methylphosphonothioic Acid (EMPTA) Using 7,7, 8,8-Tetracyanoquinodimethane (TCNO)

DETECTION PRINCIPLE

A positive test is the appearance of a blue spot in a larger pale yellow spot. If fresh reagent is not used, however, the reagent spot may be green instead of pale yellow. (With high analyte levels, the center of the blue spot may be bleached so that a white spot appears instead of a blue spot). The control (analyte level =0) and negative tests are indicated by a pale yellow spot that does not contain a blue spot in the center. The color change that is observed in a positive test is due to a sulfhydryl group in the analyte converting the 7,7,8,8-tetracyanoquinodimethane (TCNQ) reagent into a highly colored free radical. In a positive test, the color change occurs within 1 or 2 seconds after applying the TCNQ reagent.

DETECTOR REAGENT: 7, 7, 8,8-tetracyanoquinodimethane (2.5% in acetone)

PROCEDURE FOR PREPARING DETECTOR REAGENT

In a 3-ml plastic dropping bottle place 5 mg of TCNQ. Add 2 ml of acetone. Place the dropping bottle tip in place and screw on the cap. Swirl until all of the TCNQ reagent dissolves.

SOLVENT FOR THE ANALYTE: Acetone, dichloromethane, or hexane.

PREFERRED SOLID SUPPORT: MK6F Silica Gel 60A Glass Backed TLC Sheets, cat.#4861-110, Whatman Inc.

ANALYTES DETECTED WITH THIS TEST

O-ethyl methylphosphonothioic acid (EMPTA) as well as other materials containing phosphonothioic acid groups, sulfhydryl groups and other TCNQ free radical precursors.

DETECTION LIMITS FOR CWC ANALYTES

EMPTA is detectable at the 10 ng level (i.e. when a 1-microliter aliquot of an acetone solution containing 0.001% or more of analyte is spotted on preferred solid supports using a microcapillary tube).

EQUIPMENT AND MATERIALS same as Example 1 except that 7,7,8,8-Tetracyanoquinodimethane (e.g. cat. #B-7382, Sigma Chemical Co., St. Louis, Mo.) was used instead of the Bromcresol Green.

PROCEDURE same as Example 1 except that 7,7,8,8-Tetracyanoquinodimethane was used in step 7. In this example, the observation step required observing the plate for the appearance of positive tests which was indicated by the appearance of a small blue spot in a large yellow spot. The reagent spot may be green if fresh reagent is not used. A positive detection signal appears within 1–2 seconds and the colors remain stable for at least several hours.

PURPOSE AND APPLICATIONS
same as in Example 1.

EXAMPLE 3

Micro Spot Test for O-Ethyl Methylphosphonothioic Acid (EMPTA) 1,4-Dithiane, Bis(2-chloroethyl)sulfide (HD), and Bis [2-(2-ethylthio)ethyl]ether (T) Using Gold Chloride and Sodium Hydroxide

DETECTION PRINCIPLE

In this test, two detector reagents are added in sequence. The first reagent is an aqueous solution of gold chloride. The second reagent is an aqueous solution of sodium hydroxide. It is believed that the first reagent forms a brown complex with compounds containing a thioether, phosphonothioic acid group or a sulfhydryl group. The second reagent, aqueous sodium hydroxide, probably hydrolyzes the complex thereby forming gold hydroxide, which is unstable, and decomposes to gold oxide. A purplish black spot (gold oxide) in a yellow background signifies a positive test. This color change occurs at the location where the sample was spotted on the solid support. Small black speckles may also appear in the test spot. The small speckles, which occur randomly in the reagent spot should be ignored.

DETECTOR REAGENTS
1. Aqueous 4% Gold Chloride Solution
2. Aqueous 2N Sodium Hydroxide

PROCEDURE FOR PREPARING DETECTOR REAGENTS

Reagent #1

Place hydrogen tetrachloroaurate trihydrate (1 g) in a 25 ml volumetric flask and add water to the mark. Allow the solution to stand for 1 week. Place 2 ml of the solution in 2-ml plastic dropping bottle. Replace the plastic tip and screw the cover on tightly. Reagent #2

Place sodium hydroxide (8.0 grams) in a 100 ml volumetric flask. Add approximately 75 ml of water and swirl until the sodium hydroxide dissolves. Allow the solution to cool to room temperature. Add water to the mark.

SOLVENT FOR THE ANALYTE: An organic solvent (e.g. acetone, dichloromethane, hexane)

PREFERRED SOLID SUPPORT: MK6F Silica Gel 60A Glass Backed TLC Sheets, cat. #4861-110, Whatman Inc.

ANALYTES DETECTED WITH THIS TEST

O-ethyl methylphosphonothioic acid (EMPTA), Bis(2-chloroethyl)sulfide (HD), Bis[2-(2-ethylthiioethyl)]ether (T), 1,4-dithiane and other compounds containing a thioether, a phosphonothioic acid group or a sulfhydryl group.

DETECTION LIMITS FOR CWC ANALYTES

EMPTA is detectable at the 1 ng level (i.e. when a 1-microliter aliquot of an dichloromethane or hexane solution containing 0.0001% or more of analyte is spotted on the solid support using a microcap).

Dithiane is detectable at the 10 nanogram level; i.e. when a 1-microliter aliquot of a dichlormethane or hexane solution containing 0.001% or more of the analyte is spotted on the solid support using a microcap.

Bis[2-ethylthio)ethyl]ether (T) is detectable at the 10 ng level when it is applied to the thin-layer chromatographic media in hexane solution. Bis(2-chloroethyl)sulfide is detectable at the 100 ng level when it is applied to the thin-layer chromatographic media in dichloromethane solution.

EQUIPMENT AND MATERIALS

Same as those used in Example 1 except that hydrogen tetrachloroaurate (III) trihydrate (e.g. cat. #24,459-7, Aldrich Chemical Co.) and sodium hydroxide ( #22146-5, Aldrich Chemical Co.) were used instead of the Bromcresol Green.
PROCEDURE The same first six steps of example 1 were followed. Thereafter, 7. Using the dropping bottle, add 1 drop of the gold chloride reagent to each spot.
8. Wait two minutes. [EMPTA can be detected down to the 10 ng level at this point. Therefore it can be distinguished from the other analytes (that require base-step 9)].
9. Using the dropping bottle, add 1 drop of the sodium hydroxide solution to each spot.
10. Observe the plate for the appearance of a positive test. A positive test is indicated by the appearance of a small purplish black spot in a large pale yellow spot. A positive detection signal appears within 1–2 seconds and the colors remain stable for at least several hours. The test spot may contain dark speckles that appear randomly and with increasing frequency as the spot ages. These should be ignored.

EXAMPLE 4

Micro Spot Test for Bis(2-chloroethyl)sulfide (HD) Bis[2-(2-ethylthio)ethyl]ether (T), and other Mustards (including Nitrogen Mustards) Using 4-(4 '-Nitrobenzvl)pyridine and Sodium Hydroxide

DETECTION PRINCIPLE

In this test, two detector reagents are used in combination. The first reagent is a 2% solution of 4-(4'-nitrobenzyl) pyridine in an organic solvent such as denatured ethyl alcohol or toluene. The second reagent is an aqueous solution of sodium hydroxide. The thin-layer chromatographic media is heated after the 4-(4'-nitrobenzyl)pyridine is applied to the analyte spot. In the first reaction, heat accelerates the alkylation of 4-(4'nitrobenzyl)pyridine by the analyte. Basification then results in a deprotonation reaction that produces a blue dye. A positive test response is a small dark blue or purple spot on a white or pale red background.

DETECTOR REAGENTS 1. 4-(4'-Nitrobenzyl)pyridine (2%) in denatured ethanol (or toluene)
2. Aqueous 2N Sodium Hydroxide

PROCEDURE FOR PREPARING DETECTOR REAGENTS

Reagent #1

Place 4-(4"-nitrobenzyl)pyridine (20 mg) in a 2-ml plastic dropping bottle. Add 1 ml of acetone (or toluene). Swirl until the solid dissolves. Replace the plastic tip and screw the cover on tightly.

Reagent #2

Place sodium hydroxide (8.0 grams) in a 100 ml volumetric flask. Add approximately 75 ml of water and swirl until the sodium hydroxide dissolves. Allow the solution to cool to room temperature. Add water to the mark.

SOLVENT FOR THE ANALYTE: Acetone, dichloromethane, or hexane.

PREFERRED SOLID SUPPORT: MK6F Silica Gel 60A Glass Backed TLC Sheets, cat # 4861-110, Whatman, Inc.

ANALYTES DETECTED WITH THIS TEST

Bis(2-chloroethyl)sulfide (HD), Bis[2-(2-ethylthio)ethyl] ether (T), as well as other sulfur- and nitrogen-mustards. Other alkylating agents (e.g. diethyl sulfate) will also be detected.

DETECTION LIMITS FOR CWC ANALYTES

Bis [2-ethylthio)ethyl]ether (T) is detectable at the 10 ng level when it is applied to the thin-layer chromatographic media in hexane solution. Bis(2-chloroethyl)sulfide is detectable at the 100 ng level when it is applied to the thin-layer chromatographic media in dichloromethane solution.

EQUIPMENT AND MATERIALS

Same as those used in Example 1 except that 4-(4'-nitrobenzyl)pyridine (e.g. cat. #1,420- 4, Aldrich Chemical Co.) and sodium hydroxide (#22146-5), Aldrich Chemical Co.) instead of bromcresol green.

PROCEDURE

The same first six steps of example 1 were followed. Thereafter,

7. Using a dropping bottle, add 1 drop of the 4-(4"-nitrobenzyl)pyridine reagent.
8. Place the thin-layer chromatographic plate on a hot plate set at 90 degrees Centigrade. Wait for two minutes.
9. Remove the thin-layer chromatographic plate from the hot plate and allow it to cool for 15–30 seconds.
10. Using the dropping bottle, add 1 drop of the sodium hydroxide solution to each spot.
11. Observe the plate for the appearance of a positive test. A positive test is indicated by the appearance of a small blue or purple spot on a white or pale red background. A positive signal appears within 15 seconds and the colors remain stable for at least several hours.

EXAMPLE 5

Micro Spot Test for Alkyloxy Methylphosphonic Acids Using 1,3-Dicyclohexylcarbodiimide and M-272 Detector Kit Ticket for Cholinesterase Inhibitors In this example, there is provided a method for detecting the presence of alkyloxy methylphosphonic acids. In a positive test, a dehydrating reagent, 1,3-dicyclohexylcarbodiimide, reacts with an alkyloxy methylphosphonic acid (a non-inhibitor) in the sample causing elimination of a molecule of water from two molecules of the acid and results in the formation of an acid anhydride or "pyro-acid" (a cholinesterase inhibitor). The nerve agent ticket from the U.S. Army M-272 Detector Kit for Waterborne Chemical Agents is then used to determine if a cholinesterase inhibitor was formed in the reaction. The enzyme disc is observed for a positive response immediately after the enzyme disc is separated from the substrate disc. In a positive test, the enzyme disc of the M-272 detector ticket contains a white spot that covers 60% or more of the surface area of the enzyme disc. In a negative test, the enzyme disc of the M-272 detector ticket is either entirely blue or contains a white spot that covers 50% or less of the surface area of the enzyme disc.

When this test is used, the interest is mainly in determining if the level of analyte present in the sample unknown exceeds the lower limit of detection of the test. One way to determine if the test response is positive is to visually estimate the area-percentage of the enzyme disc that is white. When the enzyme disc is 60% or more white, the test response is "positive". While it is possible to quantify the level of analyte present in the sample unknown by instrumentally measuring the blue color in the enzyme disc, only a qualitative result (a go/no-go interpretation) is necessary in preferred aspects of the invention, i.e. when the test is used in chemical warfare treaty inspection applications.

The preferred solvent for carrying out this test is acetone while the preferred solid support is the Silica Gel IB, Flexible Sheets for Thin Layer Chromatography, Cat. J. T. Baker, Inc., Phillipsburg, N.J. 08865.

A factor limiting the detection sensitivity of this test is that 1,3dicyclohexylcarbodiirnide is a weak cholinesterase inhibitor (or it denatures the enzyme and hence behaves like a weak cholinesterase inhibitor. Thus, the "control" (analyte level =0) contains a white spot that covers up to 50% of the area of the cholinesterase disc. Therefore, it is anticipated that the detection sensitivity of this test can be improved significantly if: (a) a dehydrating agent that does not have an adverse effect on the enzyme is used in place of 1,3-dicyclohexylcarbodiimide or (b) the 1,3-dicyclohexylcarbodiimide is separated from the product of the reaction prior to testing the product of the reaction for anticholinesterase activity. 1,3-Dicyclohexylcarbodiimide can easily be separated from the product of the reaction by eluting the thin-layer chromatography plate (the solid support on which the test is carried out) with a solvent such as dichloromethane.

ANALYTES DETECTABLE ethyl methylphosphonic acid (EMPA), isopropyl methylphosphonlc acid (IMPA), pinacolyl methylphosphonlc acid (PMPA), cyclohexyl methylphosphonic acid (CMPA), O-ethyl methylphosphonothioic acid (EMPTA) as well as other alkyloxy methylphosphonic acids.

DECTECTION FOR CWC ANALYTES

EMPA and IMPA can be detected at the 100 ng level (i.e. when a 1-microliter aliquot of an acetone solution containing 0.01% or more of anlayte is spotted on the solid support using a microcap.

EMPTA and CMPA can be detected at the 1 microgram level (i.e. when a 1-microliter aliquot of an acetone solution containing 0.1% or more of the analyte is spotted on the solid support using a microcap.

PMPA can be detected at the 40 microgram level (i.e. when four 1-microliter aliquots of an acetone solution containing 1% or more of the analyte is spotted on the solid support using a microcap.

The detection sensitivity of this test is affected by temperature. When the test is carried out, the temperature of the test is controlled by holding the ticket in the fist while the detection reactions are carried out. Alternatively, if the temperature is controlled using a constant temperature bath, the test temperature can be decreased and the detection sensitivity of the test can probably be improved significantly.

EQUIPMENT AND MATERIALS a. Locking Forceps or Spotting Bulb Assembly for holding microcap b. Microcap, 1-microliter c. Dropping Bottle, 3-ml capacity d. Syringe, 10-microliter (e.g. cat. # 7681B52. Thomas Scientific, Boston, Mass.)

e. 1,3-Dicyclohexylcarbodiimide (1.0 M solution in dichloromethane) (e.g. cat. # 37911-5, Aldrich Chemical Co.)

f. Silica Gel IB, Flexible Sheets for Thin Layer Chromatography, Cat. 4462-02, J. T. Baker, Inc., Phillipsburg, N.J. 08865 f. Nerve Agent Detector Ticket, Water Testing Kit, Chemical Agents, M272, NSN 6665-01-134-0885 g. Scissors h. Pencil

PROCEDURE

1. Cut a the solid support to size (¼ inch square) and put a dot near the center of the support with a pencil.

2. Lock a 1-microliter microcap in the tip of the locking forceps.

3. Place tip of microcap in a sample of pure acetone and wait a few seconds for the solvent to be drawn by capillary action to fill the microcap.

4a. Place the tip of the microcap in contact with the silica gel surface of a 0.25 inch x0.25 inch piece of the solid support at a point on the support that was previously marked with a pencil. Allow a few seconds for the solvent to evaporate. This is the control (analyte level =0).

4b. (This step should only be conducted when step 4a. alone does not provide adequate results). Repeat the spotting procedure 3 more times using 1-microliter aliquots of acetone. Allow the solvent to evaporate after each application. This is the "control" (analyte level =0).

5. Using the syringe, withdraw 2 microliters (4 microliters if 4 microliters of analyte solution is used) of the carbodiimide solution from the septum-sealed bottle and add it to the sample that was spotted on the solid support. Allow the reaction to proceed for the required length of time (3 minutes).

6. Run the Enzyme Ticket Test (see below).

7. Repeat steps 1–6 using the acetone solution of the sample unknown instead of pure 5 acetone.

Enzyme Ticket Test

1. Remove the M272 Kit Nerve Agent Detector Ticket from its package. Fold back the silver foil and wet the white (enzyme) patch with a drop of water from a 3-ml dropping bottle.

2. Place the 0.25 inch x0.25 inch section of the solid support that is to be tested for anticholinesterase activity on the enzyme disc. The solid support should be applied to the enzyme disc so that the sample unknown comes in contact with the disc.

3. Cover the solid support with the silver foil and use the clip from the M-272 Kit to insure and maintain contact. Hold ticket in fist for 3 minutes (for temperature control).

4. Remove the clip and pull the silver foil completely off, thereby exposing the substrate disc.

5. Re-wet the enzyme (white) disc and fold the ticket so that both discs come in contact.

6. Clip the ticket and hold in fist for 3 minutes (for temperature control).

7. Remove the clip and observe the color of the enzyme disc. If the test is positive, 60% or more of the area of the enzyme disc will be white (the remainder will be blue). In a negative test, 50% or less of the area of the enzyme disc will be white (the remainder will be blue).

PURPOSE AND APPLICATIONS

This micro spot test method can be used as a field test for detecting alkyloxymethylphosphonic acids. It provides evidence for or against the presence of CWC analyses in a sample unknown. This test can be used alone or in conjunction with other micro spot tests that detect other functional groups in a sample unknown.

EXAMPLE 6

Micro Spot Test for Methylphosphonic Acid and Methylphosphonofluoridic Acid Using Sodium Carbonate, Diethyl Sulfate, and 1.3-Dicyclohexylcarbodiimide and then the M-272 Detector Kit Ticket for Cholinesterase Inhibitors Methylphosphonic acid and Methylphosphonofluoridic acid need to be converted into cholinesterase inhibitors in order to obtain positive tests. This is accomplished by reacting the sample unknown with (1) sodium carbonate, (2) diethyl sulfate, (3) hydrochloric acid (vapor), and (4)1,3-dicyclohexylcarbodiimide.

A factor limiting the detection sensitivity of this test is that 1,3-dicyclohexylcarbodiimide is a weak cholinesterase inhibitor (or it denatures the enzyme and hence behaves like a weak cholinesterase inhibitor) and hence, the "control" (analyte level =0) contains a white spot that covers up to 50% of the area of the enzyme disc. Therefore, the detection sensitivity of this test can be improved significantly if (a) a dehydrating agent that does not have an adverse effect on the enzyme is used in place of 1,3-dicyclohexylcarbodiimide or (b) the 1,3-dicyclohexylcarbodiimide is separated from the product of the reaction prior to testing the product of the reaction for anticholinesterase activity. 1,3-Dicyclohexylcarbodiimide can easily be separated from the product of the reaction by eluting the thin-layer chromatography plate (the solid support on which the test is carried out) with a solvent such as dichloromethane. When this procedure is used the "control" (analyte level =0) is entirely blue. Therefore, when a sample unknown is tested, any white spot in the enzyme disc would indicate that a cholinesterase inhibitor was present in the sample. Hence, detection sensitivity would be improved substantially compared with tests carried out without the special procedure that removes the 1,3-dicyclohexylcarbodiimide from the vicinity of the analyte spot.

DETECTION PRINCIPLE (1) Methylphosphonic acid is converted into its sodium salt by reacting it with sodium carbonate. (2) The sodium salt of ethylmethyl phosphonic acid is then formed by a reacting the sodium salt of ethylmethyl phosphonic acid with diethyl sulfate. (3) The product of reaction 2 is acidified. (4) A dehydrating reagent 1,3-dicyclohexylcarbodiimide, is then reacted with the alkyloxymethylphosphonic acid causing the formation of an acid anhydride or "pyro-acid" (a cholinesterase inhibitor). The nerve agent ticket from the U.S. Army M-272 Detector Kit for Waterborne Chemical Agents is then used to determnine if a cholinesterase inhibitor was formed in the reaction. In a positive test, the enzyme disc on the M-272- ticket is 60% or more white, indicating that the cholinesterase was inhibited. In a negative test, the same procedure results in cholinesterase disc that contains up to 50% white area (the remainder is blue). The blue color indicates that the enzyme was not inhibited and, therefore, was capable of hydrolyzing the substrate, indoxyl acetate, which leads to the formation of indigo. The same sequence of reactions results in a cholinesterase inhibitor being formed from methylphosphonofluoridic acid. The last two reactions (with hydrochloric acid and then with 1,3-dicyclohexylcarbodiimide) are probably not necessary when the analyte is methylphosphonofluoridic acid, but they do not interfere with the test and are useful for determining other analytes.

SOLVENT FOR THE ANALYTE: An organic solvent (e.g. acetone).
PREFERRED SOLID SUPPORT FOR THE TEST: C18 Reversed Phase TLC Plates (e.g. cat. # 4803-110 MKC18F Reversed Phase Plates, 200 micron thickness, Whatman Chemical Separation Division, Clifton, N.J. 07014).
ANALYTE DETECTABLE
Methylphosphonic acid (MPA)
EQUIPMENT AND MATERIALS
Most of the equipment from Example 4 was used in this Example as well. However, the following ingredients were also used: Sodium carbonate (e.g. cat. X 20,442-0, Aldrich Chemical Co.), Diethyl sulfate (e.g. cat #DIO,070-6, Aldrich Chemical Co.), Hydrochloric Acid (concentrated) and the following adsorbent substrate was used:

C18 Reversed Phase TLC Plates (e.g. cat. # 4803-110 MKC18F Reversed Phase Plates, 200 micron thickness, Whatman Chemical Separation Division, Clifton, N.J. 07014).
PROCEDURE
1. With a pencil section the 1 inch×3 inch TLC plate into three 1 sections.
2. Lock a 1-microliter microcap in the tip of the locking forceps.
3. Place tip of microcap in a sample of pure acetone and wait a few seconds for the solvent to be drawn by capillary action to fill the microcap.
4. Place the tip of the microcap in contact with the adsorbent surface of a 1 inch×1 inch section of the solid support at a point on the support that was previously marked with a pencil. Wait a few seconds for the solvent to evaporate. At the same location spot the solid support with a second 1-microliter quantity of acetone. This is the "control" (analyte level=0) spot.
5. Allow a few seconds for the solvent to evaporate.
6. Add one drop of 1% aqueous solution of sodium carbonate solution from a dropping bottle to the area of the solid support marked with a pencil. Wait for 1 minute.
7. Using a 10-microliter syringe add, add 1 microliter of 1% diethylsulfate in dichloromethane solution to the mark on the solid support.
8. Place the adsorbent surface of the solid support over a 200-ml beaker containing ca. 1 ml of concentrated HCl. Allow the HCl vapor to contact the solid support for 1 minute.
9. Using the syringe, withdraw 2 microliters of the 1,3-dicyclocarbodiimide solution from the septum-sealed bottle and add it to the sample that was spotted on the solid support. Wait 1 minute.
10. Perform a test with the enzyme ticket (see Example 4) to determine if a cholinesterase inhibitor formed as a result of reactions.
11. Repeat steps 1–10 using the acetone solution of the sample unknown instead of pure acetone.
PURPOSE AND APPLICATIONS
Same as that set forth in Example 5.

What is claimed is:
1. A method of detecting the presence of chemical warfare a gents, precursors and degradation products thereof, consisting of:
  contacting a liquid sample suspected of containing a member of the group consisting of chemical warfare agents, chemical warfare agent precursors, chemical warfare agent degradation products and mixtures thereof with a sufficient amount of a chromnatographic adsorbent material and a sufficient amount of a chromogemic detector reagent, wherein said contacting comprises applying said sample via a microcapillary tube to said chromatographic adsorbent,
  whereby a chromogenic indicator is formed when said sample contains said member of said group.
2. The method of claim 1, wherein said sample comprises a solution.
3. The method of claim 1, wherein said contacting comprises reacting from about 0.1 to about 10 microliters of said sample with said chromatographic adsorbent material and said chromogenic detector reagent.
4. The method of claim 1, wherein said contacting comprises reacting from about 0.5 to about 5 microliters of said sample with said chromatographic adsorbent material and said chromogenic detector reagent.
5. The method of claim 1, wherein said contacting comprises reacting from about 1 to about 3 microliters of said sample with said chromatographic adsorbent material and said chromogenic detector reagent.

6. The method of claim 1, wherein said member is selected from the group consisting of ethyl N,N-dimethylphosphoramidocyanate (GA), isopropyl methylphosphonofluoridate (GB), pinacolyl methylphosphonofluoridate (GD), cyclohexyl methylphosphonofluoridate (GF), O-ethyl S-(2-diisopropylamino)ethyl methylphosphonothiolate (VX), bis(2-chloroethyl)sulfide (HD), bis[2-(2-chloroethylthio)ethyl]ether (T), 2-chlorovinyldichloroarsine (L), methylphosphonic difluoride (DF), ethyl 2-(diisopropylamino)ethyl methylphosphonite (QL), isopropyl methylphosphonic acid (IMPA), pinacolyl methylphosphonic acid (PMPA), cyclohexyl methylphosphonic acid (CMPA), methylphosphonofluoridic acid (MPFA), methylphosphonic dichloride (DC), S-(2-diisopropylamino)ethyl methylphosphonothioic acid (EA 2192), ethyl methylphosphonic acid (EMPA), O-ethyl methylphosphonothioic acid (EMPTA), 1,4-dithiane (DITHANE), 2-chlorovinylarsenious oxide (L-OXIDE) and methylphosphonic acid (MPA).

7. The method of claim 1, wherein said chromogenic detector reagent is selected from the group consisting of bromcresol green, 7,7,8,8-tetracyanoquinodimethane, (TCNQ), gold chloride, gold chloride/ NaOH solution, cholinesterase/indoxyl acetate, 4-(4'-nitrobenzyl) pyridine/NaOH, sodium pyrophosphate peroxide/aromatic amine, o-dianisidine/sodium perborate, potassium bismuth iodide, 1,3-diisonitrosoacetone guanidinium salt, bis(diethylamino) benzophenone oxime, bis(diethylamino)benzophenone, bis(dimethylamino)thiobenzophenone, phenylazoformic acid 2-diphenylhydrazide, diphenylcarbazone, diphenylthiocarbazone, mercuric salt, diethyldithiocarbamic acid silver salt, 2,2'-dithiobis(5-nitropyridine), molybdenum oxide in sulfuric acid, ammonium molybdate, iodine/starch, and sulfuric acid (4M).

8. The method of claim 1, wherein said microcapillary tube has a cross-sectional diameter of from about 0.05 to about 0.7 millimeters.

9. The method of claim 1, wherein said microcapillary tube has a cross-sectional diameter of from about 0.1 to about 0.4 millimeters.

10. The method of claim 1, wherein said microcapillary tube has a cross-sectional diameter of from about 0.2 to about 0.25 millimeters.

11. The method of claim 1, wherein said chromatographic adsorbent material is a thin layer chromatography plate.

12. The method of claim 11, wherein said thin layer chromatography plate includes adsorbent selected from the group consisting of silica gel and alumina.

13. The method of claim 11, wherein said thin layer chromatography plate includes backing material selected from the group consisting of glass, plastic and aluminum.

14. A kit for chromogenically detecting the presence of chemical warfare agents and degradation products thereof, consisting of:

(a) microcaapillary tube means for applying a liquid sample suspected of containing a member of the group consisting of chemical warfare agents, precursors and chemical warfare agent degradation products and mixtures thereof;

(b) a sufficient amount of a chromatographic adsorbent material; and (c) a sufficient amount of a chromogenic detector reagent.

15. The kit of claim 14, wherein said member is selected from the group consisting of ethyl N,N-dimethylphosphoramidocyanate (GA), isopropyl methylphosphonofluoridate (GB), pinacolyl methylphosphonofluoridate (GD), cyclohexyl methylphosphonofluoridate (GF), O-ethyl S-(2-diisopropylamino)ethyl methylphosphonothiolate (VX), bis(2-chloroethyl)sulfide (HD), his[2-(2-chloroethylthio)ethyl] ether (T), 2-chlorovinyldichloroarsine (L), methylphosphonic difluoride (DF), ethyl 2-(diisopropylamino)ethyl methylphosphonite (QL), isopropyl methylphosphonic acid (IMPA), pinacolyl methylphosphonic acid (PMPA), cyclohexyl methylphosphonic acid (CMPA), methylphosphonofluoridic acid (MPFA), methylphosphonic dichloride (DC), S-(2-diisopropylamino)ethyl methylphosphonothioic acid (EA 2192), ethyl methylphosphonic acid (EMPA), O-ethyl methylphosphonothioic acid (EMPTA), 1,4-dithiane (DITHANE), 2-chlorovinylarsenious oxide (L-OXIDE) and methylphosphonic acid (MPA).

16. The kit of claim 15, wherein said chromogenic detector reagent is selected from the group consisting of bromcresol green, 7,7,8,8-tetracyanoquinodimethane, (TCNQ), gold chloride, gold chloride/ NaOH solution, cholinesterase/indoxyl acetate, 4-(4'-nitrobenzyl) pyridine/NaOH, sodium pyrophosphate peroxide/aromatic amine, o-dianisidine/sodium perborate, potassium bismuth iodide, 1,3-diisonitrosoacetone guanidinium salt, bis(diethylamino) benzophenone oxime, bis(diethylamino)benzophenone, bis(dimethylamino)thiobenzophenone, phenylazoformic acid 2-diphenylhydrazide, diphenylcarbazone, diphenylthiocarbazone, mercuric salt, diethyldithiocarbamic acid silver salt, 2,2'-dithiobis(5-nitropyridine), molybdenum oxide in sulfuric acid, ammonium molybdate, iodine/starch, and sulfuric acid (4M).

17. The kit of claim 4, wherein said chromatographic adsorbent material is a thin layer chromatography plate.

18. The kit of claim 17, wherein said thin layer chromatography plate includes adsorbent material selected from the group consisting of silica gel and alumina.

19. The kit of claim 17, wherein said thin layer chromotography plate includes backing material selected from the group consisting of glass, plastic, or aluminum.

20. The kit of claim 4, wherein said means for obtaining a sample comprises a capillary tube.

21. The kit of claim 20, wherein said microcapillary tube has a cross-sectional diameter of from about 0.05 to about 0.7 millimeters.

22. The kit of claim 20, wherein said microcapillary tube has a cross-sectional diameter of from about 0.1 to about 0.4 millimeters.

23. The kit of claim 20, wherein said microcapillary tube has a cross-sectional diameter of from about 0.2 to about 0.25 millimeters.

24. The kit of claim 21, wherein said microcapillary tube is capable of delivering from about 0.1 to about 10 microliters of said sample.

25. The kit of claim 22, wherein said microcapillary tube is capable of delivering from about 0.5 to about 5 microliters of said sample.

26. The kit of claim 23, wherein said microcapillary tube is capable of delivering from about 1 to about 3 microliters of said sample.

* * * * *